(12) United States Patent
Carter et al.

(10) Patent No.: US 7,976,493 B2
(45) Date of Patent: Jul. 12, 2011

(54) DISPOSABLE INFUSION DEVICE WITH RESETTABLE LAST DOSE LOCK-OUT

(75) Inventors: Brett J. Carter, Monroe, WA (US); John M. Adams, Snohomish, WA (US)

(73) Assignee: Calibra Medical, Inc., Redwood City, CA (US)

( * ) Notice: Subject to any disclaimer, the term of this patent is extended or adjusted under 35 U.S.C. 154(b) by 178 days.

(21) Appl. No.: 12/435,996

(22) Filed: May 5, 2009

(65) Prior Publication Data

US 2010/0286602 A1    Nov. 11, 2010

(51) Int. Cl.
*A61M 31/00* (2006.01)

(52) U.S. Cl. .......................................... 604/67

(58) Field of Classification Search .................... 604/65, 604/67, 890.1, 891.1, 151–152, 154, 500
See application file for complete search history.

(56) References Cited

U.S. PATENT DOCUMENTS

| 2007/0213658 A1* | 9/2007 | Hickle | 604/66 |
| 2008/0132842 A1* | 6/2008 | Flaherty | 604/151 |

\* cited by examiner

*Primary Examiner* — Nicholas D Lucchesi
*Assistant Examiner* — Christopher D Koharski
(74) *Attorney, Agent, or Firm* — Richard O. Gray, Jr.; Graybeal Jackson LLP

(57) ABSTRACT

A wearable infusion device comprises a reservoir that holds a liquid medicament, an outlet that delivers the liquid medicament to a patient, and a pump that displaces a volume of the liquid medicament to the outlet when actuated. The device further includes a lock-out that disables actuation of the device responsive to a predetermined condition of the device. The lock-out is resettable.

17 Claims, 8 Drawing Sheets

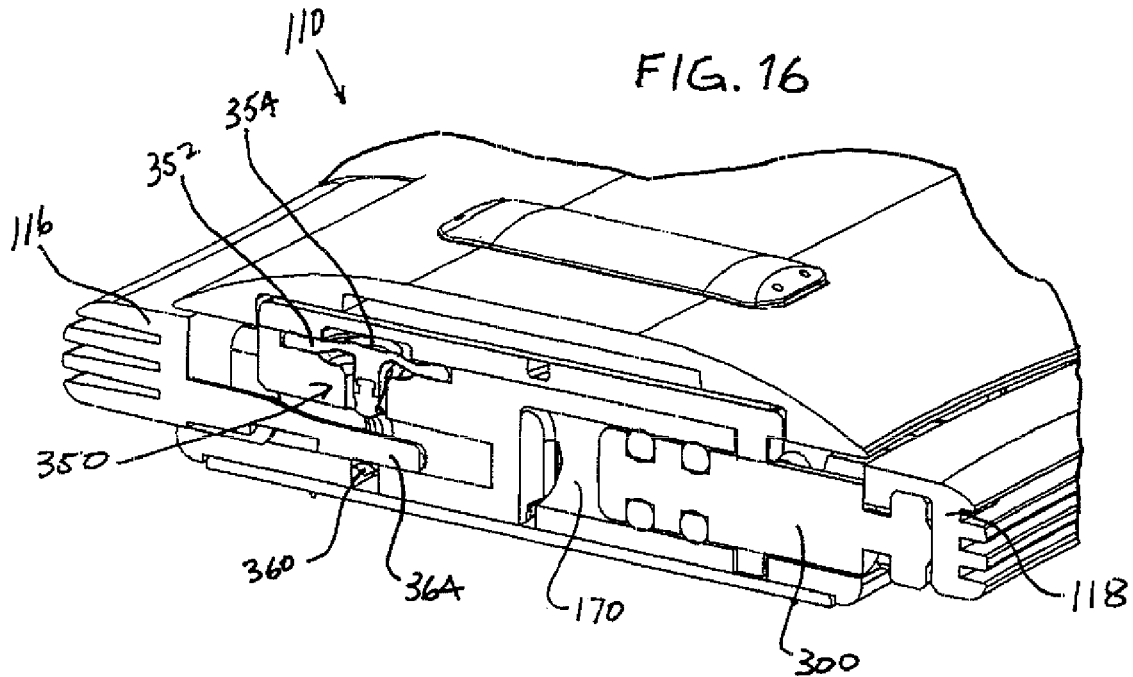
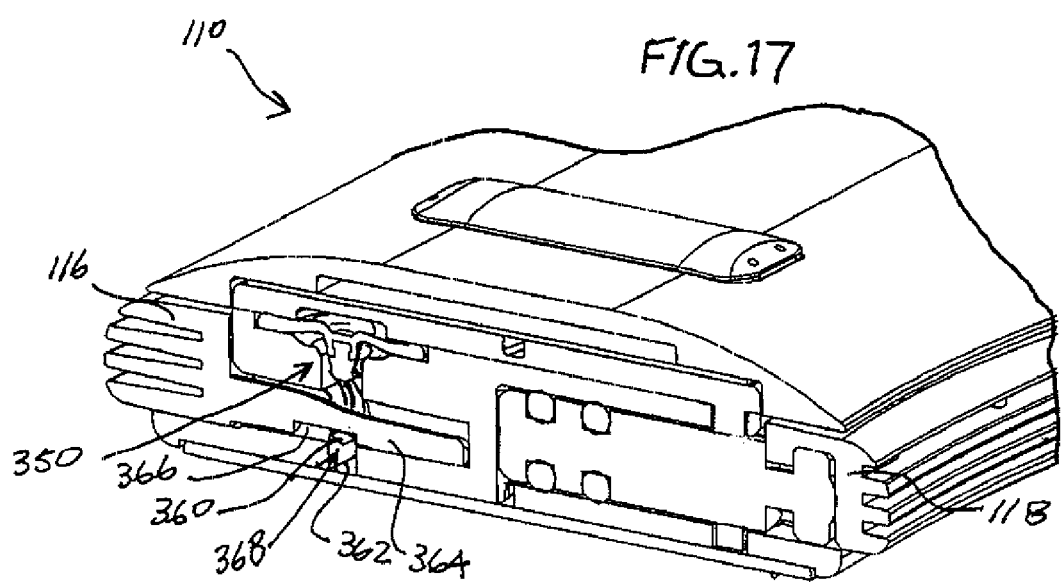

DISPOSABLE INFUSION DEVICE WITH RESETTABLE LAST DOSE LOCK-OUT

BACKGROUND OF THE INVENTION

The present invention relates to infusion devices and more particularly to such devices that enable liquid medicaments to be conveniently and safely self-administered by a patient.

Administration of insulin has traditionally been accomplished using a syringe. Recently, needle carrying pen-like devices have also been employed for this purpose. Both forms of insulin administration require the patients to stick themselves each time they inject insulin, often many times a day. Thus, these traditional forms of insulin administration have been a rather pervasive intrusion in the lives and routines of the patients who have had to adopt and employ them.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such devices may involve fewer needle sticks, they are expensive to manufacture. They are also complex to operate and cumbersome and awkward to wear. Further, the cost of such devices can be many times the daily expense of using a traditional injection means such as a syringe or an insulin pen.

Devices of the type mentioned above also require a significant amount of training to control and thus use the devices. Great care in programming the devices is required because the pumps generally carry sufficient insulin to last a few days. Improper programming or general operation of the pumps can result in delivery of an excessive amount insulin which can be very dangerous and even fatal.

Many patients are also reluctant to wear a pump device because they can be socially awkward. The devices are generally quite noticeable and can be as large as a pager. Adding to their awkwardness is their attachment to the outside of the patients clothes and the need for a catheter like tubing set running from the device to an infusion set located on the patient's body. Besides being obvious and perhaps embarrassing, wearing such a device can also be a serious impediment to many activities such as swimming, bathing, athletic activities, and many activities such as sun bathing where portions of the patient's body are necessarily uncovered.

In view of the above, a more cost effective and simple device has been proposed whereby an injection system is discreetly attached directly to the skin of the patient. The device may be attached to the patient under the patient's clothing to deliver insulin into the patient by the manual pumping of small doses of insulin out the distal end of a temporarily indwelling cannula that is made a part of the pump device. The cannula may be made a part of the drug delivery device before, during or after the attachment of the drug delivery device to the skin of the patient. The device may be made quite small and, when worn under the clothes, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For a more complete description of devices of this type, reference may be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

Devices of the type described may be intended for single use. That is, after initial filling of the device reservoir device deployment, and self-administered drug dosing to drug depletion, disposal of the device may be required. In such an event, it would be helpful to have a mechanism built into the device that prevents further use of the device after drug depletion. One solution to achieve this end is fully disclosed and claimed in U.S. co-pending application Ser. No. 11/906,104 filed Sep. 29, 2007 for DISPOSABLE INFUSION DEVICE WITH REUSE LOCK-OUT, which application is owned by the assignee of this invention and incorporated herein by reference in its entirety. As taught therein, the dose delivery actuator may be disabled upon operation of the device actuation buttons when the reservoir is empty. Unfortunately, this device disablement may accidentally occur before the device is ever deployed for use. For example, the device disablement may occur by the actuating buttons being accidentally operated prior to the filling of the device reservoir. Such accidental disablement would render the device useless.

Accordingly, the present invention provides further improvement to the devices disclosed in the above referenced co-pending application. More particularly, the present invention provides for improved patient safety and/or convenience. To that end, the invention provides, an infusion device which includes device disablement upon the reservoir becoming empty while allowing the device disablement to be reset if it occurs prior to the deployment of the device.

SUMMARY OF THE INVENTION

In one embodiment, a wearable infusion device comprises a resettable lock-out. The device includes a reservoir that holds a liquid medicament, an outlet that delivers the liquid medicament to a patient and a pump that displaces a volume of the liquid medicament to the outlet when actuated. The device further includes a lock-out that disables actuation of the device responsive to a predetermined condition of the device. The lock-out is resettable.

The lock-out is a last dose lock-out. The predetermined condition of the device may be that the reservoir is substantially empty. The device may further include a fill port communicating with the reservoir to permit liquid medicament to be introduced into the reservoir. The lock-out is resettable through the fill port.

The device may further comprise a control that actuates the pump and the lock-out may be arranged to disable the control.

The lock-out may include a pressure sensor. The predetermined condition may be a reduced pressure such as below ambient pressure, sensed by the pressure sensor. The pump may be arranged to produce the reduced pressure when the reservoir is empty. The pump may be a piston pump.

The piston pump may be arranged to produce the reduced pressure during a recharge stroke when the reservoir is empty. The device may further include a fill port communicating with the reservoir to permit liquid medicament to be introduced into the reservoir. The reduced pressure is releasable to reset the lock-out by venting the fill port. The fill port may be arranged to communicate with the reservoir to permit liquid medicament to be introduced into the reservoir and the reduced pressure may be releasable to reset the lock-out by venting the fill port and actuating the piston pump through a recharge cycle. The pressure sensor may be disposed between the pump and the reservoir.

In another embodiment, wearable infusion device comprises a reservoir that holds a liquid medicament, an outlet that delivers the liquid medicament to a patient, and a pump that displaces a volume of the liquid medicament to the outlet when actuated. The device further includes a lock-out including a pressure sensor that disables actuation of the device responsive to the pressure sensor sensing a reduced pressure. The reduced pressure is releasable to reset the lock-out.

The pump may be arranged to produce the reduced pressure when the reservoir is empty. The pump may be a piston pump. The piston pump may be arranged to produce the reduced pressure during a recharge stroke when the reservoir is empty.

The device may further include a fill port communicating with the reservoir to permit liquid medicament to be introduced into the reservoir. The reduced pressure may be releasable to reset the lock-out by venting the fill port.

The may further comprise a fill port communicating with the reservoir to permit liquid medicament to be introduced into the reservoir. The reduced pressure may be releasable to reset the lock-out by venting the fill port and actuating the piston pump through a recharge cycle. The pressure sensor may be between the pump and the reservoir.

In a further embodiment, a wearable infusion device comprises a reservoir that holds a liquid medicament, a fill port permitting a medicament to be introduced into the reservoir, an outlet that delivers the liquid medicament to a patient, and a piston pump that displaces a volume of the liquid medicament to the outlet when actuated. The piston pump is operable through a recharge cycle and produces a reduced pressure during the recharge cycle when the reservoir is empty. The device further includes a lock-out including a pressure sensor that disables actuation of the device responsive to the pressure sensor sensing the reduced pressure. The reduced pressure is releasable through the fill port to reset the lock-out.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 16 is another sectional view in perspective of the lock-out shown after the last dosage delivery; and FIG. 17 is a perspective view of the lock-out shown disabling the device after the last dosage delivery.

DETAILED DESCRIPTION OF THE INVENTION

Figure 1:
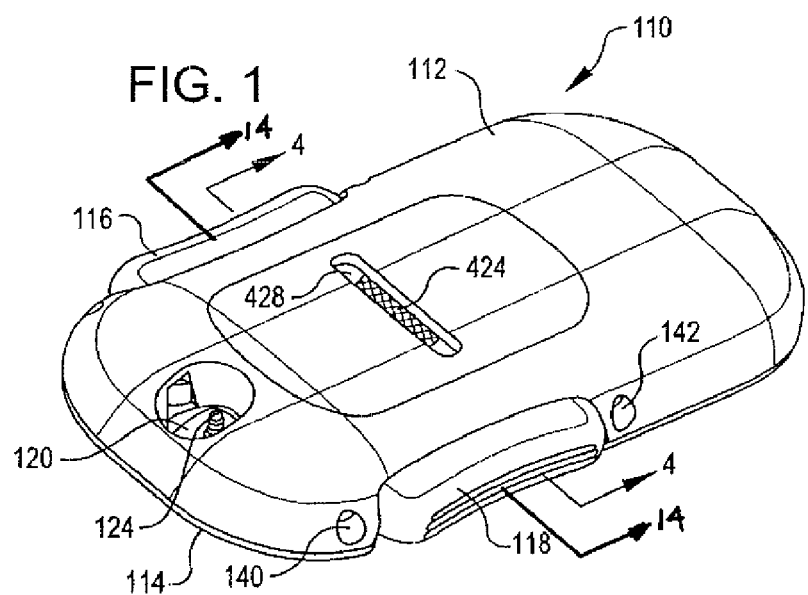
FIG. 1 is a perspective view of an infusion device embodying the present invention shown without a deployed cannula.
Figure 2:
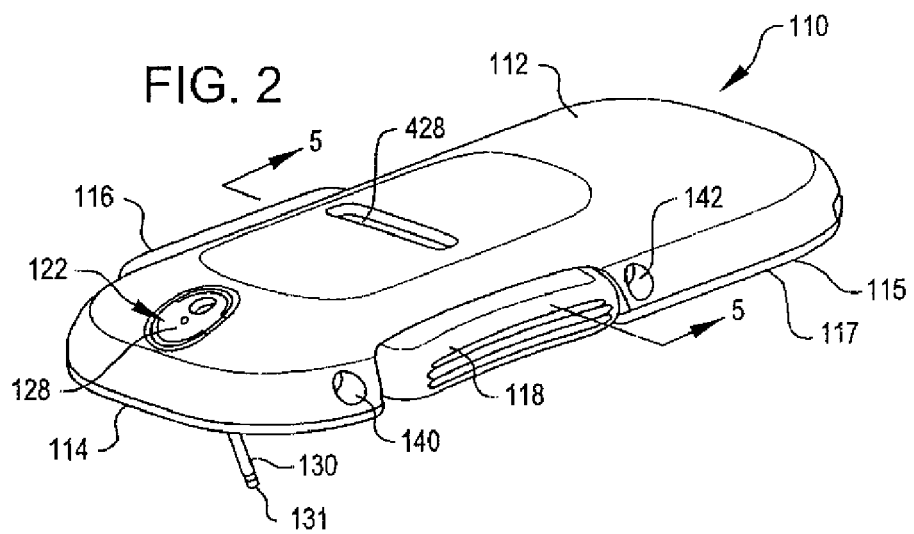
FIG. 2 is another perspective view of the infusion device of FIG. 1 shown with a deployed cannula.

Referring now to FIGS. 1 and 2, they are perspective views of an infusion device 110 embodying various aspects of the present invention. FIG. 1 shows the device prior to receiving and thus without a cannula while FIG. 2 illustrates the device after having received a cannula 130 that has a distal end 131. As may be seen in both FIGS. 1 and 2, the device 110 generally includes an enclosure 112, a base 114, a first actuator control button 116, and a second actuator control button 118.

The enclosure 112, as will be seen subsequently, is formed by virtue of multiple device layers being brought together. Each layer defines various components of the device such as, for example, a reservoir, fluid conduits, pump chambers, and valve chambers, for example. This form of device construction results in a compact design and enables manufacturing economy to an extent that the device is disposable after use.

The base 114 preferably includes a pad 115 attached to the base 114. The pad 115 has an adhesive coating 117 on the side thereof opposite the base 114 to permit the device to be adhered to a patient's skin. The adhesive coating may originally be covered with a releasable cover 292 (FIG. 13A) that may be pealed off of the adhesive layer 117 when the patient endeavors to adhere the device 110 to their skin.

The device 110, as will be seen herein after is first adhered to the patient's skin followed by the deployment of the cannula 130 thereafter. However, it is contemplated herein that various aspects of the present invention may be realized within a device that may alternatively be mated with a previously deployed cannula assembly.

The actuator buttons 116 and 118 are placed on opposites sides of the device 110 and directly across from each other. This renders more convenient the concurrent depression of the buttons when the patient wishes to receive a dose of the liquid medicament contained within the device 110. This arrangement also imposes substantially equal and opposite forces on the device during dosage delivery to prevent the device from being displaced and possibly stripped from the patient. As will be further seen hereinafter, the concurrent depression of the buttons is used to particular advantage. More specifically, the actuator button 116 may serve as a valve control which, when in a first position as shown, establishes a first fluid path between the device reservoir and the device pump to support pump filling, and then, when in a second or depressed position, establishes a second fluid path between the device pump and the device outlet or distal end of the cannula to permit dosage delivery to the patient. As will be further seen, a linkage between the control actuator buttons 116 and 118 permits actuation of the device pump with the actuator control button 118 only when the second fluid path has been established by the first actuator control button 116. Hence, the first actuator control button 116 may be considered a safety control.

The actuator buttons 116 and 118 are preferably arranged to require a complete through of their travel to achieve activation of the device pump and thus dosage delivery. This, together with the sudden release of resistance to actuator advancement creates a snap action that provides an advantage in positively knowing that dosage delivery has occurred and that no less than a full dose has been delivered. For more description regarding this feature, reference may be had to co-pending application Ser. No. 11/906,102, titled DISPOSABLE INFUSION DEVICE WITH SNAP ACTION ACTUATION, which application is owned by the assignee of this application and is incorporated herein by reference in its entirety.

As may be noted in FIG. 1, the device 110 includes a cavity 120 that is arranged to receive a cannula assembly 122 (FIG. 2) from which the cannula 130 extends. When the cannula is deployed, the outlet 124 of the device 110 is placed in fluid communication with the cannula 130 by a cannula carrier 128 of the cannula assembly 122 that carries the cannula. When thus deployed, the cannula 130 extends from the base 114 of the device 110 to beneath the skin of the user.

As may further be noted in FIGS. 1 and 2, the enclosure 112 of the device 110 includes a pair of pockets 140 and 142 on opposite sides of the second actuator button 118. A similar pair of pockets, not seen in the figure, are also provided on opposite sides of the first actuator button 116. These pockets are used to receive corresponding projections of a cannula placement assembly for releasably joining the cannula placement assembly to the device 110 to support cannula deployment as will be described subsequently. As will also be seen, upon cannula deployment, the cannula placement assembly is automatically released from the device by the driver projections being forced from the pockets.

Figure 3:
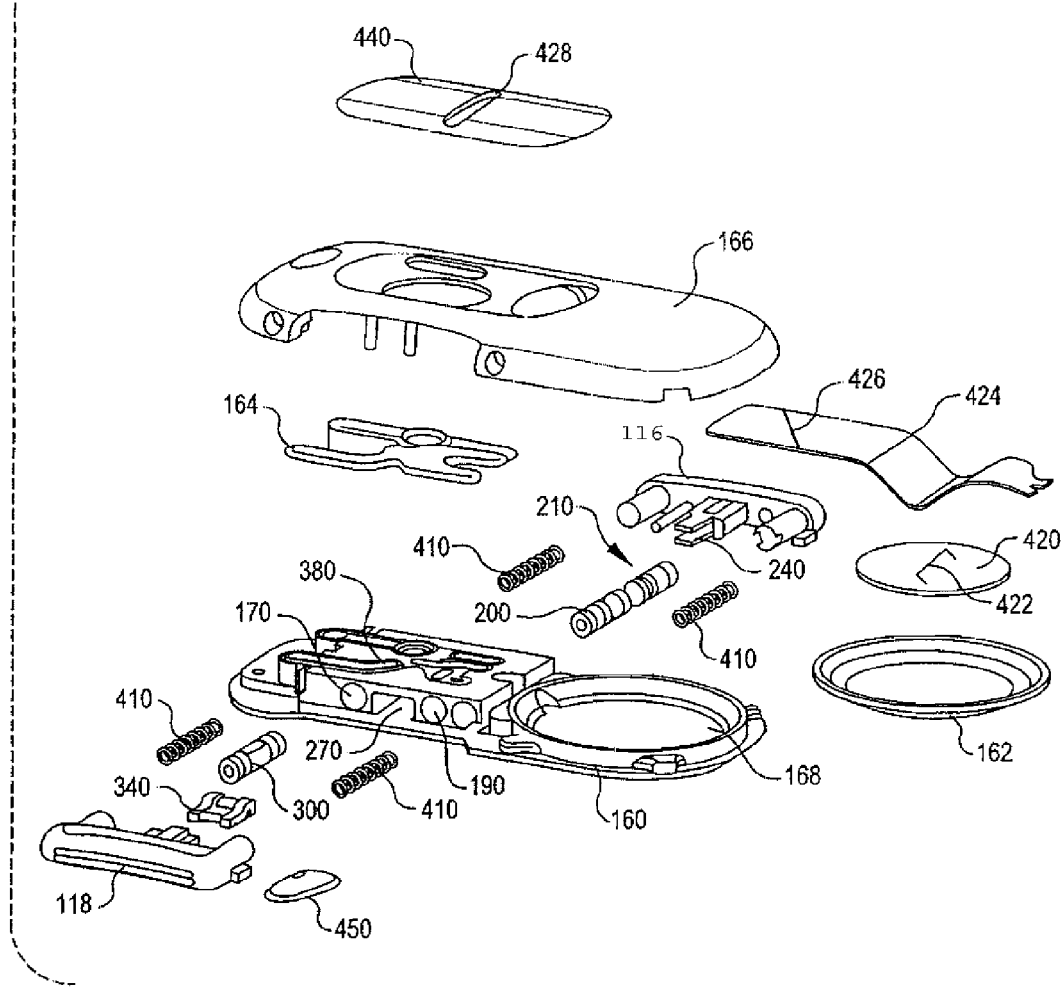
FIG. 3 is an exploded perspective view of the device of FIG. 1.

Referring now to FIG. 3, it is an exploded perspective view of the device 110 of FIG. 1. It shows the various component parts of the device. The main component parts include the aforementioned device layers including the base layer 160, a reservoir membrane 162, an intermediate layer 164 and a top body layer 166. As may also be seen in FIG. 3, the base layer 160 is a substantially rigid unitary structure that defines a first reservoir portion 168, a pump chamber 170, and a valve chamber 190 that receives a shuttle bar 200 of a shuttle valve 210. A reservoir membrane layer 162 is received over the reservoir portion 168 to form an expandable/deflatable reservoir of the device 110. The base layer 160 may be formed of plastic, for example. The base and the top body layer may be joined together, trapping the intermediate layer there between by any means such as with screws, ultrasonic welding or laser welding.

The valve chamber 190 is arranged to receive a valve shuttle bar 200 carried by and extending from the first actuator button 116. A series of O-rings, to be described subsequently, are seated on the shuttle bar 200 to form first, second, and third valves. The actuator button 116 also carries a first linkage portion 240 of the linkage that permits actuation of the device pump with the actuator control button 118 only when the second fluid path has been established by the first actuator control button 116. The first linkage portion 240 is received within a suitably configured bore 270 formed in the base layer 160 and will be described subsequently.

The pump actuator button 118 is arranged to be linked to a pump piston 300 and a second linkage portion 340 to interact with the first linkage portion 240. The pump piston 300 is arranged to be received within the pump chamber 170 and the second linkage portion 340 is arranged to be received within the bore 270 for interacting with the first linkage portion 240. O-rings are seated on the piston 300 to provide a seal against leakage and to prevent external contaminants from entering the piston chamber.

The intermediate layer 164 may be a generally resilient member and received on the base layer 160 to cover channels scribed in the base layer as a type of gasket to form fluid channels 380 that serve to conduct the medicament from the reservoir to the device outlet and to the distal end 131 (FIG. 2) of the cannula 130. Springs 410 are arranged to spring load the actuator buttons 116 and 118 away from each other.

The reservoir membrane 162 is formed of flexible membrane material and is received over the reservoir portion 168 to form the reservoir of the device 110. A rigid plate 420 is arranged to be adhered to the reservoir membrane 162 of the reservoir. Because the membrane 162 is flexible, it will move as the reservoir is filled and emptied. The rigid plate 420 will then move with it. The plate 420 includes an eyelet 422 dimensioned to receive an elongated web 424 that forms a part of a medicament level indicator. The web 424 carries an indicator line or feature 426 that may be read through a window 428 of the device top most panel 440.

Another component of the device 110 is a translucent window 450 that is received on the underside of the base 160. As will be seen hereinafter, the window forms a part of a prime indicator. It is formed of a transparent material such as glass or transparent plastic and has a roughened surface rendering it translucent. However, when it is covered with or at least wetted by liquid medicament, it is rendered essentially transparent creating a visually obvious condition and, for example, permitting indicia to be seen beneath it indicating that the conduit to the device outlet is primed and ready to deliver fixed doses of medicament when desired.

Figure 4:
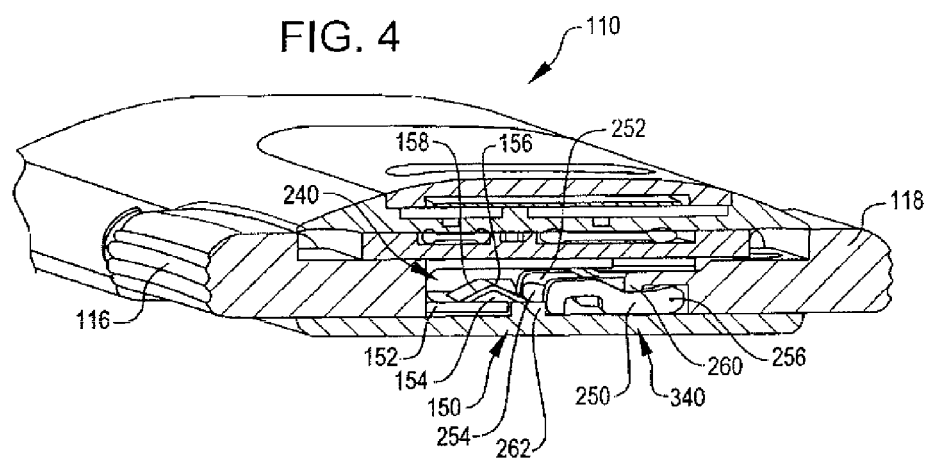
FIG. 4 is a sectional view, in perspective, to an enlarged scale, taken along lines 4-4 of FIG. 1, showing the actuation linkages of the device of FIG. 1 prior to medicament dosage delivery.
Figure 5:
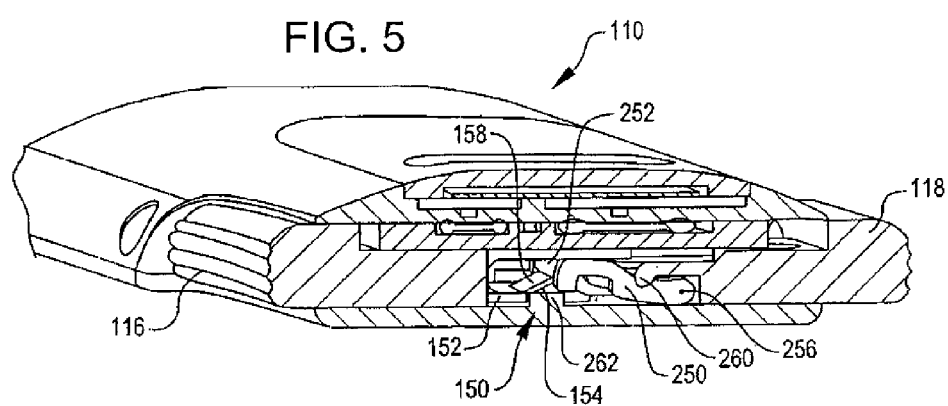
FIG. 5 is another sectional view, in perspective, to an enlarged scale, taken along lines 5-5 of FIG. 2, showing the actuation linkage operation of the device of FIG. 1 during medicament dosage delivery.
Figure 6:
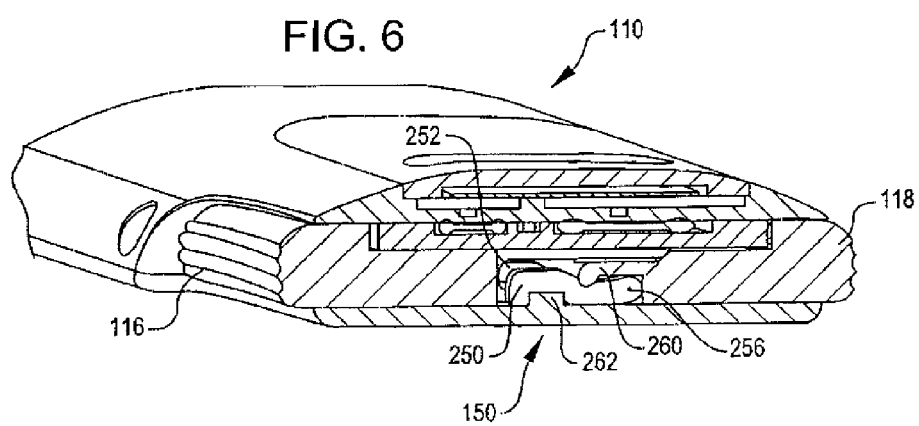
FIG. 6 is another sectional view similar to that of FIG. 5, in perspective, to an enlarged scale, showing the actuation linkage operation of the device of FIG. 1 immediately after dosage delivery.

FIGS. 4-6 show details of the operation of the linkage that permits actuation of the device pump with the actuator control button 118 only when the second fluid path from the reservoir to the outlet has been established by the first actuator control button 116. The linkage has been given the general reference character 150.

As may be seen FIG. 4, the first actuator button 116 has an extension 152 that terminates in a block 154. The block 154 has a first ramp surface 156 and a second ramp surface 158. When the device 110 is actuated, the button 116 is concurrently depressed with pump button 118. It and its extension 152 and block 154 are free to move to the right. As seen in FIGS. 4 and 5, the pump actuator button 118 has parallel extensions 250 and 252 which are joined and separated be a rod member 254. The extensions 250 and 252 are pivotally mounted to pivot about a pivot point 256. Another extension 260 of the pump actuator button 118 spring biases the extensions 250 and 252 as shown in FIG. 4. As seen in FIG. 4, the extensions 250 and 252 abut an abutment 262 which they must clear to enable the actuator 118 to be moved to the left. As shown in FIG. 5, as the button 116 is depressed, its extension 152 moves to the right causing the first ramp surface 156 to engage the rod member 254. Continued movement of the button causes the rod member 254 to ride up the first ramp surface 156 which in turn causes the extensions 250 and 252 to begin to move slightly to the left and bend upward against the loading of extension 260. Eventually, the rod member 254 rides up the length of the first ramp 156 and down the second ramp 158 causing the extensions 250 and 252 to clear the abutment 262 and continue their travel to the left until the extensions are received on the opposite side of the abutment as shown in FIG. 6. The pump button 116 has now been fully depressed to deliver a dose of measured medicament. When the ends of extensions 250 and 252 totally clear the abutment 262, they will snap behind the abutment 262 as shown in FIG. 6 and become temporarily locked. Meanwhile, the rod member 254 has traversed all the way down the second ramp surface 158. The buttons 116 and 118 are now fully depressed.

Hence, from the above, it may be seen that the pump button 118 could not at first move freely while the first actuator button 116 which operates the valves could. As a result, the pump actuation lags behind the valve actuation. This enables the device outlet to be sealed from the reservoir and the pump connected to the outlet before the pump is permitted to pump any medicament to the outlet. Hence, the device establishes a medicament delivery flow path to the cannula before the pump is able to begin pumping the medicament to the patient. Thus, it is assured that there is never an open unobstructed pathway between the reservoir and the fluid outlet. Also, by assuring that the pump only draws fluid from the reservoir when the pathway to the outlet is sealed off, it is also assured that a precise amount of fluid is moved with each pump cycle. This operation is completely timed by the linkage just described and occurs quickly, appearing to the patient that both actuator buttons are moving at the same rate.

When the extensions 250 and 252 of the pump button clear the abutment 262, they become locked in a snap action. This provides positive feedback to the patient that a dosage of medicament was delivered as desired. It also causes a full dose to be delivered. By virtue of the snap action of the pump actuator, only full doses may be administered.

When the medicament has been delivered, the spring loading of the actuator buttons returns the buttons to their first or initial position. During this time, the same timing provided by the block 154 is used for recharging the pump. More specifically, ramp 158 unlatches the ends of extensions 250 and 252 by lifting rod member 254. While the extensions 250 and 252 are being lifted by the ramp 158, the valve control button 116 is returning to the left to cause the outlet to be disconnected from the pump before the reservoir is reconnected to the pump for charging, thus sealing the outlet from both the pump and the reservoir before the reservoir is connected to the pump for recharging. This assures that the pump does not pull medicament from the patient but only from the reservoir. As the pump returns, a full dose of the medicament is drawn up into the piston chamber 170 to ready the device for the next dosage delivery.

Figure 7:
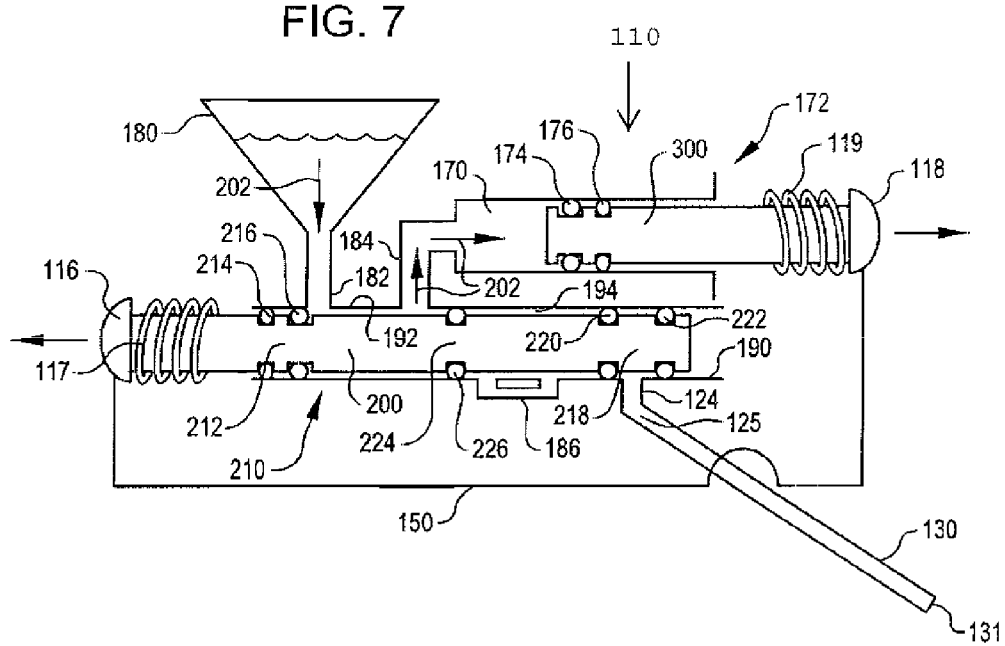
FIG. 7 is a schematic representation of the valves and pump of the device of FIG. 1 between medicament dosage deliveries and during the filling of the pump with the medicament.
Figure 8:
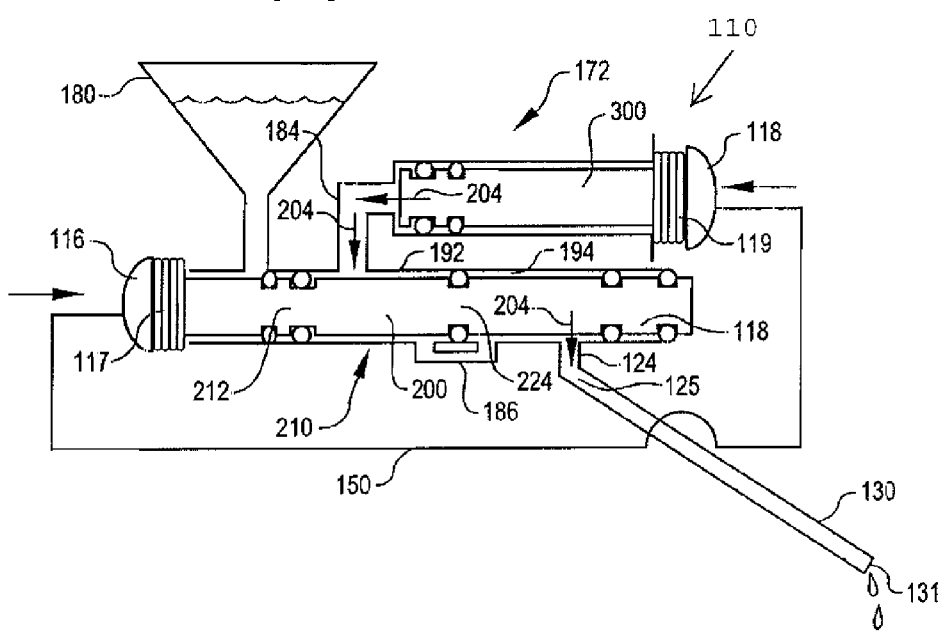
FIG. 8 is another schematic representation of the valves and pump of the device of FIG. 1 during medicament dosage delivery.

Referring now to FIGS. 7 and 8, they are schematic representations of the valves and pump of the device of FIG. 1 between medicament dosage filling (FIG. 7) and medicament dosage delivery (FIG. 8). As may be seen in FIGS. 7 and 8, the device 110 further includes a reservoir 180, a pump 172, and the cannula 130. The reservoir 180 may be formed as shown in FIG. 3 by the combination of the device base 160 and the flexible membrane 162. The device further includes the shuttle valve 210 including shuttle bar 200. The shuttle bar 200 is shown within the valve chamber 190. The shuttle bar 200 and O-rings 214 and 216 form a first valve 212, shuttle bar 200 and O-rings 220 and 222 form a second valve 218 and shuttle bar 200, O-ring 226 and a bypass channel 186 form a third valve 224. Although O-rings are used herein to form seals, other types of valve construction may employ forms of seals other than O-rings without departing from the invention.

The pump piston 300 is within the piston camber 170 to form a piston pump 172. The actuator control button 118 is directly coupled to and is an extension of the pump piston 300. It may also be noted that the actuator buttons 116 and 118 are spring loaded by springs 117 and 119, respectively. The springs are provided for returning the actuator buttons to a first or start position after a dosage is administered.

A fluid conduit 182 extends between the reservoir 180 and the valve 212. An annular conduit 192 extends between the O-rings 216 and 226, and an annular conduit 194 extends between the O-rings 226 and 220. A fluid conduit 184 provides a fluid connection between the reservoir 180 and the annular conduits 192 and 194 depending upon the position of the shuttle valve 210. Also illustrated in FIG. 7 is the linkage 150 that assures that the shuttle valve 210 is actuated before the piston pump 172 is actuated to provide a dose of medicament.

In FIG. 7, the valves are shown in a first configuration immediately after having returned to their first position following a dosage delivery. After the return of the valves, the linkage 150 permits the pump actuator 118 and piston 300 to return for refilling the pump chamber 170 in ready for the next medicament dosage delivery. During their return, the medicament flows as indicated by arrows 202 from the reservoir 180, through the conduit 182, through the annular channel 192, through conduit 184, and into the pump chamber 170.

As may be noted, when in the first position, the valves 218 and 224 isolate the outlet 124 from both the reservoir 180 and the piston pump 118. Having two such valves isolate the outlet 124 when the valves are in the first configuration provides an added degree of safety from medicament being inadvertently delivered to the patient between dosage deliveries. For example, this provides additional safety that the liquid medicament is not accidentally administered to the patient notwithstanding the inadvertent application of pressure to the reservoir. In applications such as this, it is not uncommon for the reservoir to be formed of flexible material. While this has its advantages, it does present the risk that the reservoir may be accidentally squeezed as it is worn. Because the valves 218 and 224 isolate the outlet 124 when the valves are in their first configuration, this redundant protection assures that pressure, accidentally applied to the reservoir, will not cause the fluid medicament to flow to the cannula.

In addition to the linkage 150 preventing return of the piston 300 until after the valves return to their first and start positions, the O-rings on the shuttle bar 200 are also spaced apart to insure that the valves 218 and 224 isolate the outlet 124 from the pump 172 and reservoir 180 before the pump is again connected to the reservoir. The O-ring spacing thus effectively forms a second linkage to assure that the cannula 130 is connected to the pump 172 only when a dosage is to be delivered and that it is never connected to the reservoir 180.

In operation, the pump chamber 170 is first filled as the actuator button 118 returns to the first position after having just delivered a medicament dosage. In this state, the shuttle valve 210 is set so that the first valve 212 will be open and the second and third valves 218 and 224 will be closed. This establishes a first fluid path indicated by arrows 202 from the reservoir 180 to the pump chamber 170 to fill the piston pump 172. When the patient wishes to receive another dose of medicament, the actuator buttons are concurrently pressed. The aforementioned linkages, including linkage 150, cause the first valve 212 to close and the second and third valves 218 and 224 to thereafter open. Meanwhile, actuation of the pump 172 is precluded until the first valve 212 is closed and the second and third valves 218 and 224 are opened. At this point a second fluid path indicated by arrows 204 is established from the pump chamber 170 to the cannula 130. The medicament is then administered to the patient through the distal end 131 of cannula 130.

Once the medication dosage is administered, the piston 300, and thus the actuator button 118, is returned under the spring pressure of spring 119 to its initial position. During the travel of the piston back to its first position, a given volume of the liquid medicament for the next dosage delivery is drawn from the reservoir into the pump chamber 170 as described above to ready the device for its next dosage delivery.

Figure 9:
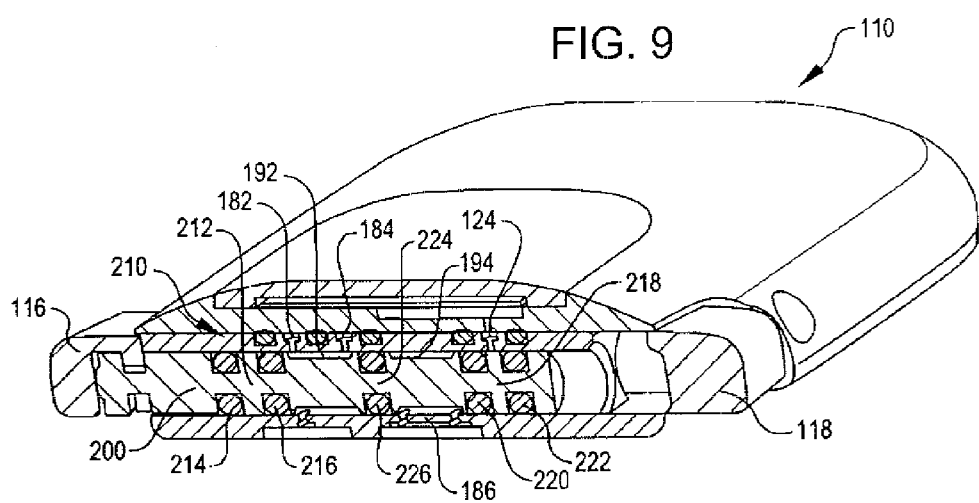
FIG. 9 is a sectional view, in perspective, to an enlarged scale, showing the configuration of the valves of the device of FIG. 1 during pump filling and prior to medicament dosage delivery.

Referring now to FIG. 9, it is a sectional view in perspective showing the valve configuration of the device 110 of FIG. 1 during medicament filling of the pump chamber 170 immediately after a dosage delivery. Here, it may be clearly seen that the first actuator button 116 is directly coupled to the shuttle bar 200 of the valves 212, 218, and 224. Above the valves are the conduits from the reservoir, from the pump, and to the cannula. More particularly, the conduit 182 is in fluid communication with the reservoir, the conduit 184 is in fluid communication with the pump, and the conduit 124 is in fluid communication with the cannula. The valves are shown with the first valve 212 opened, communicating reservoir conduit 182 with the pump conduit 184 through channel 192, the second valve 218 closed and blocking the conduit 124 to the cannula, and the third valve 224 closed and blocking both the reservoir conduit 182 and the pump conduit 184 from the cannula conduit 124. This permits medicament to flow from the reservoir through conduit 182, through channel 192, and to the pump chamber 170 through conduit 184 as the actuator button 116 returns to its first position. Hence, the pump chamber is filled and ready for the next dosage delivery.

Figure 10:
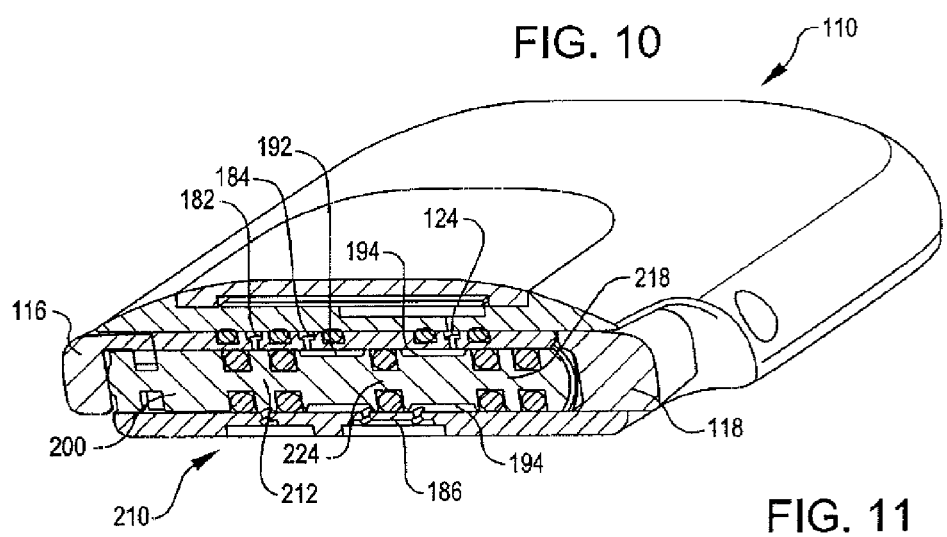
FIG. 10 is another sectional view, in perspective, to an enlarged scale, showing the configuration of the valves of the device of FIG. 1 during dosage delivery.

Referring now to FIG. 10, it is a sectional view in perspective similar to that of FIG. 9 but showing the valve configuration of the device 110 of FIG. 1 during medicament delivery. Here, the valves are shown with the first valve 212 closed and blocking the reservoir conduit 182, the second valve 218 opened permitting the outlet conduit 124 to communicate with the annular conduit 194, and the third valve 224 opened permitting medicament to flow from the annular conduit 192, through bypass 186, and to annular conduit 194. Thus, medicament is permitted to flow from the pump conduit 184, through annular conduit 192, through the bypass 186, through annular conduit 194, and into the outlet conduit 124 to administer the fixed volume dosage. As previously mentioned, the O-rings defining the first valve 212, the third valve 224, and the second valve 218 are spaced apart so that conduit 182 is blocked before conduits 184 and 124 are connected together through the valves 224 and 218.

Figure 11:
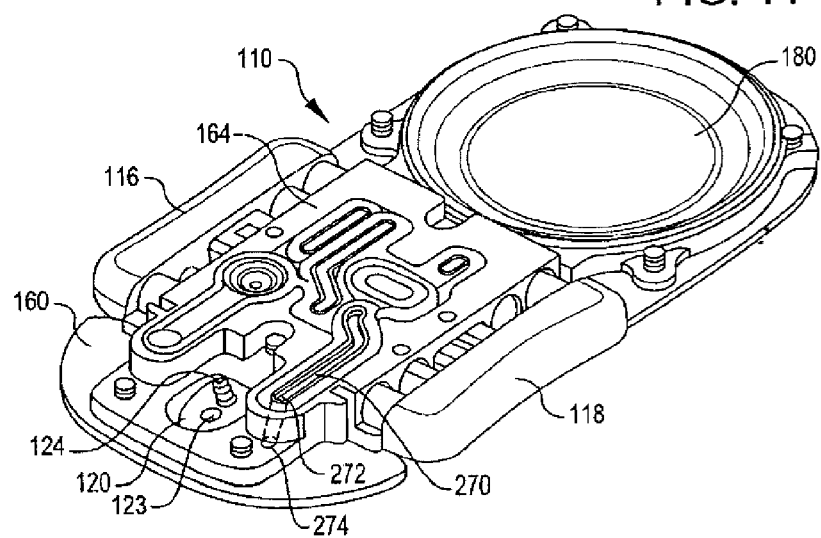
FIG. 11 is a top perspective view of the base of the device of FIG. 1 illustrating various fluid paths within the device.
Figure 12:
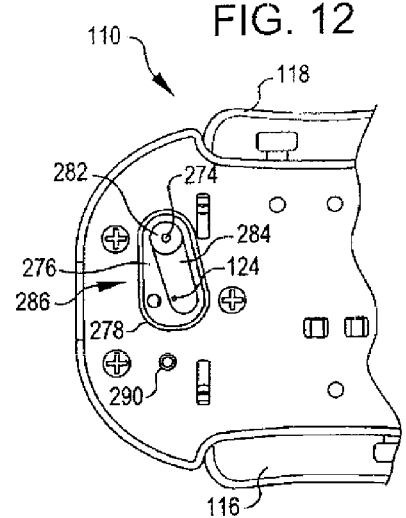
FIG. 12 is a partial bottom plan view of the base of the device of FIG. 1 to illustrate the interior of a prime indicator according to one embodiment thereof.

FIG. 11 is a top perspective view of the base 160 of the device 110 of FIG. 1. Carried on the base 160 is the intermediate layer 164. Together, the base 160 and intermediate layer 164 define numerous fluid conduits within the device 110. One such fluid conduit is designated with reference character 270 in FIG. 11. The conduit 270 is within the fluid path that leads to the outlet 124. It is in the downstream portion of that path and takes a bend at 272 towards the bottom side of the base 160 where it, through an opening 274, enters a chamber 276 (FIG. 12). The chamber 276 communicates with the device outlet 124 that projects into the aforementioned cavity 120. When the cannula 130 (FIG. 13) is placed, it extends through an opening 123 in the cavity to beneath the patient's skin and communicates with the outlet 124 as described herein after.

Figure 13:
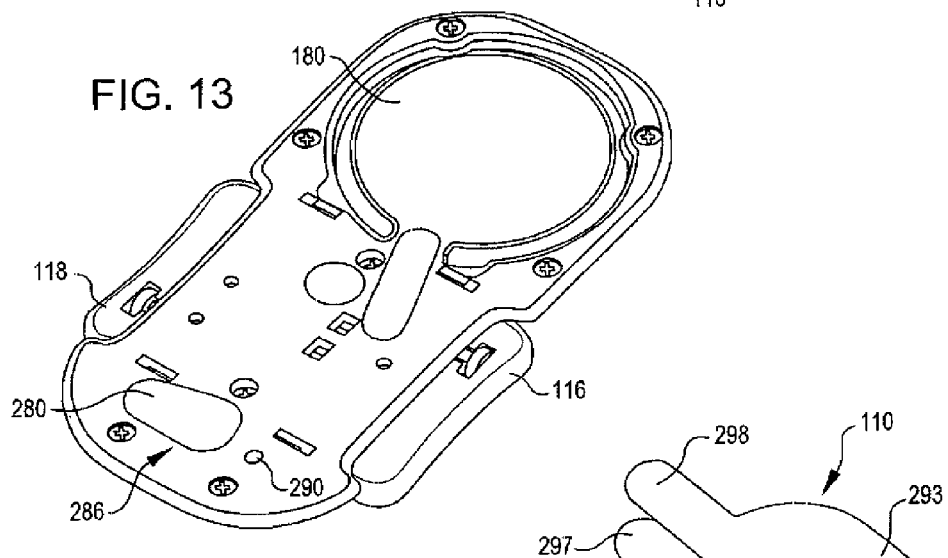
FIG. 13 is a bottom plan view of the base of the device of FIG. 1 illustrating the prime indicator interior covered by a translucent cover according to the above mentioned prime indicator embodiment.

The chamber 276 is partly defined by a seal rim 278 which receives a translucent cover 280 (FIG. 13). The top wall of the chamber 276 has an inverted cone shaped surface 282 portion and a tapered portion 284 to the outlet 124.

The translucent cover may be formed of transparent plastic wherein the surface that faces the chamber is roughed in a manner that renders the plastic cover translucent. The upper surface of the chamber is preferably coated with indicia which may, for example, be a color, such as blue. When the chamber is empty, the blue indicia will not be readily seen because the rough surface of the cover has rendered the cover translucent. However, when the chamber 276 is filled with a liquid, such as the liquid medicament, the cover 280 will become more transparent allowing the blue indicia to be readily seen. The chamber 276 and cover 280 thus form a prime indicator 286 adjacent the outlet 124. More particularly, the prime indicator 286 is immediately adjacent the outlet 124 since when the chamber is filled and the indicia readily seen, it will be known that the conduits and cannula are sufficiently prime with medicament to permit a full dosage to be delivered upon the next activation of the device 110.

In use, it is contemplated that the reservoir be filled through a fill port 290 on the bottom of the device 110 before the device is deployed on the patient's skin. After the device is filled, the translucent cover or window 280 may be viewed during device priming. During the priming process, the actuators 116 and 118 may be depressed a number of times until the blue indicia on the top surface portions 282 and 284 of the chamber are seen through the window 280. This provides an indication to the user that the chamber 276, and more importantly, the conduits are sufficiently primed and full with medicament to enable actual dosage delivery upon the next actuation of the device 110. Hence, a prime indicator 286 is provided immediately adjacent the outlet 124.

Figure 13A:
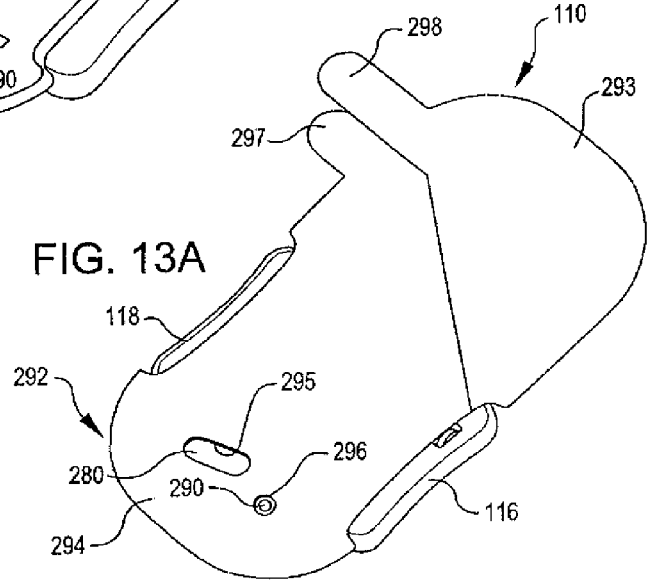
FIG. 13A is a bottom view of the device 110 illustrating a removable non-adhesive layer overlying an adhesive layer on the device base.

In FIG. 13A, it may be seen that the removable non-adhesive layer 292, in accordance with this embodiment, includes two portions, a first portion 293 and a second portion 294. Each of the first and second layer portions 293 and 294, respectively, includes a tab 298 and 297 respectively that extend beyond the margins of the device base. This permits the tabs 297 and 298 to be grasped for effortless removal of the removable non-adhesive layer portion 294 and 293. The layer portion 293 includes cutouts. The cutouts 295 and 296 extend through the pad 115 (FIG. 2) to provide access to the device fill port 290 and the prime indicator window 280. Hence, as described above, the device 110 may be filled and primed for use before the removable layer portions 293 and 294 are removed for adhering the device to a patient's skin.

Figure 14:
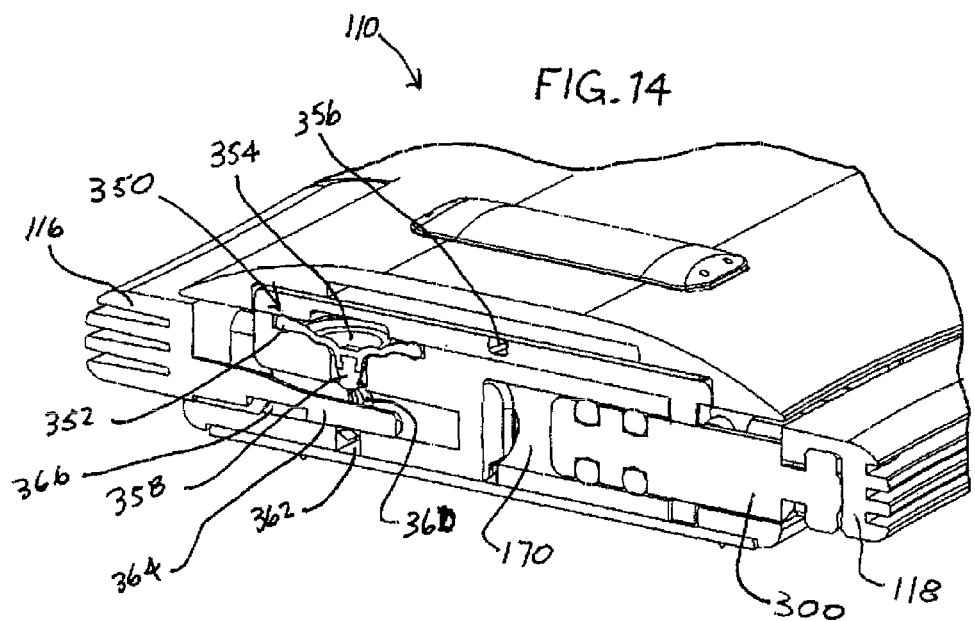
FIG. 14 is a sectional view, in perspective, taken along lines 14-14 of FIG. 1 of a lock-out according to an embodiment of the device of FIG. 1 shown prior to an intended dosage delivery.

FIGS. 14-17 are sectional views in perspective of a resettable lock-out 350 according to an embodiment of the present invention. More particularly, as will be seen subsequently, the lock-out 350 is a last dose lock-out that is resettable if the lock-out occurs prior to deployment of the device 110. FIG. 14 shows the lock-out 350 prior to an intended dosage delivery.

When the pump chamber 170 is filled with medicament as the actuator button 118 returns during a recharge stroke after the immediately preceding dosage delivery, medicament flows from the reservoir through a conduit 356 to the pump chamber 170. A diaphragm chamber 354 is in fluid communication with this flow path from the reservoir to the pump chamber 170. The diaphragm chamber 354 is defined by a diaphragm 352 formed of flexible membrane material. The diaphragm 352 includes an extension 358 that terminates in a hook portion 360. The distal end of the hook portion 360 lies within a slot 362. As long as there is medicament within the diaphragm chamber 354, the hook portion 360 will remain in the slot 362.

The first actuator button 116 includes an extension 364. The extension 364 includes a slot 366. When the first actuator button 116 is fully depressed, the slot 366 of the extension 364 will be alignment with the slot 362. As will be seen subsequently, if there is no medicament within the diaphragm chamber 354 during a pump recharge stroke, the hook enters the slot 366 and remains there to disable the device by locking the actuator buttons. As also shall be seen, this locking arrangement is resettable.

Figure 15:
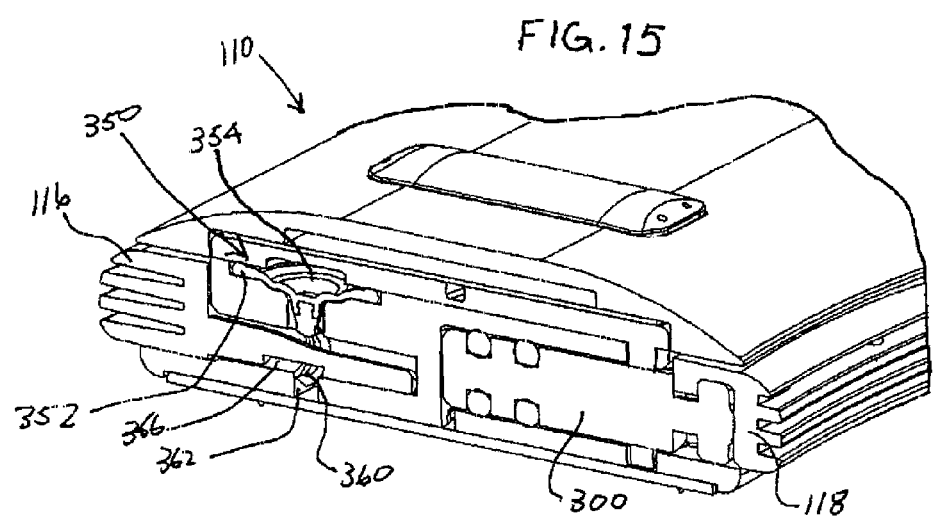
FIG. 15 is another sectional view, in perspective, of the lock out shown during a last dosage delivery.

FIG. 15 shows the lock-out 350 during a normal dosage delivery, such as the dosage delivery before the last dosage delivery. The pump piston 300 has displaced medicament from the pump chamber and the slot 366 is aligned with the slot 362. The hook portion 360 remains in the slot 362.

FIG. 16 shows the lock-out 350 after the dosage delivery before the last dosage delivery. The reservoir and diaphragm chamber 354 are made empty during the recharge stroke of the pump piston 300. Because the reservoir and diaphragm chamber 354 are empty, a negative pressure within the diaphragm chamber 354 is pulled by the piston 300 as it returns during its last recharge stroke that fills the pump chamber for the last dosage delivery. The negative pressure within the diaphragm chamber 354 causes the diaphragm 352 to be pulled up into the diaphragm chamber 354. The hook portion 360 is also pulled up with the diaphragm 352 and contacts the underside of the extension 364. The device 110 is now ready for lock-out during the last dosage delivery.

FIG. 17 shows the lock-out upon completion of the last dosage delivery. As may be noted, the hook portion 360 is pulled up into the slot 366 of the extension 364. The capture of the hook portion 360 by the slot 366 precludes the actuator buttons 116 and 118 from returning to their initial positions. Further actuation of the device 110 has been locked-out.

Upon each recharge cycle, a small negative pressure is caused when the reservoir is not empty. However, this small negative pressure is very small and short lived compared to when the reservoir is empty. Hence, the lock-out will occur when the pressure within the diaphragm chamber 354 is less than a predetermined pressure below ambient pressure.

As previously mentioned, if the device has not yet been deployed, and lock-out occurs, the lock-out 350 may be reset. To reset the lock out, it is only necessary to release the negative pressure in the diaphragm chamber 354 to return the diaphragm to its original shape for releasing the hook portion 360 from the slot 366. This may be accomplished by venting the reservoir through the fill port 290 (FIG. 13A).

To that end, the fill port may be packed with a septum formed of a membrane penetrable by a needle, for example. To reset the lock out, such a needle may be used to penetrate the septum within the fill port 290 to admit air or medicament into the reservoir of the device 110. That air or medicament will flow into the diaphragm chamber 354 to release the pressure within the diaphragm chamber 354, permitting the diaphragm 352 to return to its original shape and to allow the hook portion 360 to exit the slot 366 and return to the slot 362. With the last dose lock-out 350 now reset, the reservoir may be filled with medicament and used normally.

While particular embodiments of the present invention have been shown and described, modifications may be made. It is therefore intended in the appended claims to cover all such changes and modifications which fall within the true spirit and scope of the invention as defined by those claims.

What is claimed is:

1. A wearable infusion device comprising:
a reservoir that holds a liquid medicament;
an outlet that delivers the liquid medicament to a patient;
a pump that displaces a volume of the liquid medicament to the outlet when actuated; and
a lock-out that disables actuation of the device responsive to a predetermined condition of the device, the lock-out being resettable,
wherein the lock-out includes a pressure sensor and the predetermined condition is a reduced pressure sensed by the pressure sensor,
wherein the device further comprises a fill port communicating with the reservoir to permit liquid medicament to be introduced into the reservoir and wherein the reduced pressure is releasable to reset the lock-out by venting the fill port.

2. The device of claim 1, wherein the lock-out is a last dose lock-out.

3. The device of claim 1, further comprising a control that actuates the pump and wherein the lock-out disables the control.

4. The device of claim 1, wherein the reduced pressure is below ambient pressure.

5. The device of claim 1, wherein the reduced pressure is less than a predetermined pressure below ambient pressure.

6. The device of claim 1, wherein the pump produces the reduced pressure when the reservoir is empty.

7. The device of claim 1, wherein the pump is a piston pump.

8. The device of claim 7, wherein the piston pump produces the reduced pressure during a recharge stroke when the reservoir is empty.

9. The device of claim 1, wherein the pressure sensor is between the pump and the reservoir.

10. A wearable infusion device comprising:
a reservoir that holds a liquid medicament;
an outlet that delivers the liquid medicament to a patient;
a piston pump that displaces a volume of the liquid medicament to the outlet when actuated; and
a lock-out that disables actuation of the device responsive to a predetermined condition of the device, the lock-out being resettable,
wherein the lock-out includes a pressure sensor and the predetermined condition is a reduced pressure sensed by the pressure sensor,
the device further comprising a fill port communicating with the reservoir to permit liquid medicament to be introduced into the reservoir and wherein the reduced pressure is releasable to reset the lock-out by venting the fill port and actuating the piston pump through a recharge cycle.

11. A wearable infusion device comprising:
a reservoir that holds a liquid medicament;
an outlet that delivers the liquid medicament to a patient;
a pump that displaces a volume of the liquid medicament to the outlet when actuated; and
a lock-out including a pressure sensor that disables actuation of the device responsive to the pressure sensor sensing a reduced pressure, the reduced pressure being releasable to reset the lock-out, the device further comprising a fill port communicating with the reservoir to permit liquid medicament to be introduced into the reservoir and wherein the reduced pressure is releasable to reset the lock-out by venting the fill port.

12. The device of claim 11, wherein the pump produces the reduced pressure when the reservoir is empty.

13. The device of claim 11, wherein the pump is a piston pump.

14. The device of claim 11, wherein the pressure sensor is between the pump and the reservoir.

15. The device of claim 13, wherein the piston pump produces the reduced pressure during a recharge stroke when the reservoir is empty.

16. A wearable infusion device comprising:
   a reservoir that holds a liquid medicament;
   an outlet that delivers the liquid medicament to a patient;
   a piston pump that displaces a volume of the liquid medicament to the outlet when actuated; and
   a lock-out including a pressure sensor that disables actuation of the device responsive to the pressure sensor sensing a reduced pressure, the reduced pressure being releasable to reset the lock-out, the device further comprising a fill port communicating with the reservoir to permit liquid medicament to be introduced into the reservoir and wherein the reduced pressure is releasable to reset the lock-out by venting the fill port and actuating the piston pump through a recharge cycle.

17. A wearable infusion device comprising:
a reservoir that holds a liquid medicament;
a fill port permitting a medicament to be introduced into the reservoir;
an outlet that delivers the liquid medicament to a patient;
a piston pump that displaces a volume of the liquid medicament to the outlet when actuated, the piston pump being operable through a recharge cycle and producing a reduced pressure during the recharge cycle when the reservoir is empty; and
a lock-out including a pressure sensor that disables actuation of the device responsive to the pressure sensor sensing the reduced pressure, the reduced pressure being releasable through the fill port to reset the lock-out.

* * * * *